United States Patent
Cho et al.

(10) Patent No.: US 10,124,104 B2
(45) Date of Patent: Nov. 13, 2018

(54) DIALYSATE REGENERATION UNIT AND BLOOD DIALYZING APPARATUS HAVING THE SAME

(71) Applicants: Taebeom Cho, Daejeon (KR); Kyungsoo Lee, South Burlington, VT (US)

(72) Inventors: Taebeom Cho, Daejeon (KR); Kyungsoo Lee, South Burlington, VT (US)

(73) Assignee: Human Biomed, Inc

( * ) Notice: Subject to any disclaimer, the term of this patent is extended or adjusted under 35 U.S.C. 154(b) by 38 days.

(21) Appl. No.: 15/309,790

(22) PCT Filed: May 8, 2015

(86) PCT No.: PCT/KR2015/004578
§ 371 (c)(1),
(2) Date: Nov. 8, 2016

(87) PCT Pub. No.: WO2015/170900
PCT Pub. Date: Nov. 12, 2015

(65) Prior Publication Data
US 2017/0143887 A1    May 25, 2017

(30) Foreign Application Priority Data
May 8, 2014  (KR) .................. 10-2014-0054504

(51) Int. Cl.
*A61M 1/16* (2006.01)
*A61M 1/36* (2006.01)
(Continued)

(52) U.S. Cl.
CPC ........ *A61M 1/1696* (2013.01); *A61M 1/1603* (2014.02); *A61M 1/1662* (2014.02);
(Continued)

(58) Field of Classification Search
CPC combination set(s) only.
See application file for complete search history.

(56) References Cited

U.S. PATENT DOCUMENTS 4,079,007 A * 3/1978 Hutchisson ............. A61M 1/16
                                              210/321.71
4,218,541 A * 8/1980 Ackerman .......... A61M 1/1696
                                              210/611
(Continued)

FOREIGN PATENT DOCUMENTS

JP   10-085324 A      4/1998
KR   10-2008-0064448  7/2008
KR   10-2010-0101101  9/2010

OTHER PUBLICATIONS

International Search Report for PCT/KR2015/004578, dated Aug. 27, 2015.

*Primary Examiner* — Dirk R Bass
(74) *Attorney, Agent, or Firm* — Lee & Associates, LLC (57) ABSTRACT

Provided is a temperature-based dialysate regeneration device for regulating a temperature of dialysate discharged from a hemodialyzer to remove uremic toxins and waste therefrom, the temperature-based dialysate regeneration device including: a Joule-Thomson refrigerator, including a compressor, condenser, expander and evaporator, an adsorbent column, and a dialysate heat exchanger in which heat transfer occurs between dialysates. The refrigerant used for the JT refrigerator may be a mixture of two or more refrigerants to enhance the heat transfer generated by the latent heat in the evaporator and the condenser.

14 Claims, 7 Drawing Sheets (51) Int. Cl.
*F25B 6/04* (2006.01)
*B01D 15/36* (2006.01)
*F25B 1/00* (2006.01)
*A61M 1/34* (2006.01)
*B01D 61/24* (2006.01)
*C12M 1/12* (2006.01)

(52) U.S. Cl.
CPC ........ *A61M 1/3403* (2014.02); *A61M 1/3472* (2013.01); *A61M 1/3679* (2013.01); *B01D 15/363* (2013.01); *B01D 61/243* (2013.01); *C12M 1/12* (2013.01); *F25B 1/00* (2013.01); *F25B 6/04* (2013.01); *A61M 2205/3368* (2013.01); *A61M 2205/3372* (2013.01); *A61M 2205/36* (2013.01); *A61M 2205/3606* (2013.01); *B01D 2311/103* (2013.01); *B01D 2311/106* (2013.01); *B01D 2311/25* (2013.01); *B01D 2311/2626* (2013.01); *B01D 2313/38* (2013.01); *B01D 2313/40* (2013.01); *F25B 2339/047* (2013.01)

(56) References Cited

U.S. PATENT DOCUMENTS

| | | |
|---|---|---|
| 6,530,234 B1 | 3/2003 | Dobak, III et al. |
| 2014/0014580 A1 | 1/2014 | Ritter |

* cited by examiner

DIALYSATE REGENERATION UNIT AND BLOOD DIALYZING APPARATUS HAVING THE SAME

CROSS-REFERENCE TO RELATED APPLICATIONS

This application is a national stage application of International Patent Application No. PCT/KR2015/004578 filed on May 8, 2015, which claims priority to Korean Patent Application No. 10-2014-0054504 filed on May 8, 2014, the entire contents of which are incorporated by reference herein.

TECHNICAL FIELD

The present invention generally relates to a blood dialyzing apparatus to remove waste in blood by circulating blood and dialysate while interposing a hemodialysis filter therebetween, and more particularly, to a temperature-based dialysate regeneration device configured to regenerate used dialysate using a mixed refrigerant Joule-Thomson refrigerator and an adsorbent column, and a blood dialyzing apparatus having the same.

BACKGROUND

When there is a kidney dysfunction, water and waste products that have to be discharged out of body accumulate in blood and imbalance of electrolytes and hormones in the body occurs. Renal failure patients are continuously increasing during last decades, resulting in the significant increase in the national medical expenses and the shortage of medical staffs for renal failure patients.

Most commonly performed to improve such a kidney failure symptom is hemodialysis which is to circulate blood out of body and rid the blood of the accumulated uremic toxin and excess water by a semi-permeable dialysis membrane. Hemodialysis is a method of seeking an electrolyte balance and ridding the body fluid of uremic toxin and excess water, taking advantages of diffusion applied due to the concentration difference and filtration applied due to the pressure difference between blood and dialysate.

For the hemodialysis, a patient visits a hemodialysis center 2-4 times every week and receives hemodialysis treatment which is usually performed for three to six hours. 140 to 200 liters of dialysate is used for each hemodialysis treatment. The dialysate used in the hemodialysis is formed of ultrapure water having no bacteria and virus that can be transmitted to the patient's blood through a hemodialyzer. Thus, a dialysate supply apparatus may include various filtration steps, such as a pre-filtration unit, a water softener, a reverse osmosis filter, and a water sterilization function. Considering that approximately 300 liters of tap water is required to produce 140 liters of reverse osmotic ultrapure water, it is inevitable that a dialysate supply apparatus should be enlarged.

Such in-center hemodialysis occupies more than 80% of entire dialytic therapies. However, it has been reported that the five-year survival rate of renal failure patients on hemodialysis is even below 50%. Hemodialysis patients cannot help following certain dietary restrictions like water control, phosphorus control and protein metabolism. Also, considering a hemodialysis schedule, patients are restricted to leave their community or pursue career and social activities. Ultimately, the quality of life of renal-failure patients on hemodialysis declines hugely.

As a method for overcoming such disadvantages of in-center hemodialysis, much attention has been paid to portable hemodialysis which uses a small and light dialysis device, which can be directly carried or used by a patient. The portable hemodialysis allows patients to receive dialysis treatment when and where they want. In addition, the dialysis treatment can be performed more frequently and the imbalance in the body water level can be corrected more often, alleviating the dietary restrictions. In addition, there are no limits on dialysis places such that patients receiving the portable hemodialysis may travel and move freely enough to improve the quality of their life.

Recent clinical research also shows that daily hemodialysis can reduce cardiovascular complications, increase uremic toxin removal and decrease pre-dialytic uremic toxin levels, which ultimately leads to a lowered mortality risk, as compared with conventional thrice-weekly hemodialysis. As it allows the patient to perform the dialysis in a third place or at home, the portable hemodialysis also contributes for the redistribution of medical staffs necessary for the hemodialysis center. Accordingly, the portable hemodialysis provides various advantages in the patients' social as well as physiological standpoint, compared with the in-center hemodialysis.

Despite such advantages, the portable hemodialysis is performed limitedly because it is difficult for patients to manufacture and manage 140 liters or more of ultrapure dialysate. As mentioned above, considering that more than 300 liters of tap water is required to produce 140-200 liters of ultrapure water, it is practically impossible for patients to produce and manage such a large amount of ultrapure water at home or while traveling. Accordingly, dialysis regeneration draws a great interest because it enables a small amount of dialysate to be continuously reused during hemodialysis. In order to regenerate dialysate, small—(e.g., urea nitrogen, creatinine and phosphoric acid) and middle-sized molecules (e.g., beta 2-microglobulin) are removed from the used dialysate, and pH and conductivity are adjusted. The dialysate regeneration provides various advantages in hemodialysis therapy. The amount of water can be minimized enough to reduce the size of the dialysis device. The cost for hemodialysis may also be reduced, which can eventually reduce financial burdens of the national medical expenditure.

One dialysate regeneration apparatus commercialized is a sorbent filter manufactured by Renal Solutions. The sorbent filter includes four layers for dialysate regeneration, including activated Carbon, Urease, Zirconium Phosphate, and Zirconium Oxide and Zirconium Carbonate. The activated carbon adsorbs and removes diverse sizes of molecules from the dialysate, except urea nitrogen which is a small molecule. Ureases convert the urea nitrogen into ammonia and carbonate ions. Zirconium Phosphate acts as a cation exchanger and removes ammonia, calcium and magnesium ions. On the contrary, Zirconium Oxide and Zirconium Carbonate acts as an anion exchanger to remove phosphate and fluoride. However, the sorbent filter cannot be used together with the citrate anticoagulant which is required for some renal failure patients, because of an aluminum detection problem. Various chemical problems have also been reported.

The dialysate regeneration can also be achieved by physical adsorption performed by an adsorbent, excluding the various chemical bonding described in the sorbent filter. The adsorbent such as the activated charcoal can adsorb diverse sizes of molecules. However, it is known that an adsorption efficiency of the small-sized molecules including urea nitrogen existing largely in the used dialysate is substantially low. However, it has been reported that the adsorption rate of the urea nitrogen by an activated charcoal can be increased by lowering the dialysate temperatures. For example, when a dialysate of 37° C. which is a body temperature is flowing through the activated charcoal, it is identified that 4.5 g of urea nitrogen per 1 kg of activated charcoal is adsorbed. Once the dialysate temperature is lowered to 1° C., the adsorption rate of the urea markedly increases and 11.28 g of urea nitrogen are adsorbed on the same amount of the activated charcoal. Thus, cold dialysate regeneration which uses that the urea nitrogen adsorption is increased at low temperature and the desorption of the urea nitrogen occurs at high temperatures is introduced.

Korean patent application is also published that discloses 'Cold dialysate regeneration system with carbon and nano-fiber column' (Korean Patent Publication No. 2008-006448) which uses such cold dialysate regeneration. However, there is a big hurdle in the effort to achieve a large variation of the dialysate temperature in the published disclosure because the dialysate temperature is regulated using a Peltier device. In addition, such the patent application has a disadvantage of being a large-sized dialysate regeneration device and cannot pursue the objectives of a small and light-weighted dialysate regeneration apparatus which is essential for the portable hemodialysis.

SUMMARY OF THE DISCLOSURE

The present invention provides a temperature-based dialysate regeneration device and a blood dialyzing apparatus including the temperature-based dialysate regeneration device, which can regulate the temperature of dialysate quickly and regenerate the dialysate by using a mixed-refrigerant Joule-Thomson refrigerator.

Embodiments of the present invention provide a blood dialyzing apparatus for purifying blood, the blood dialyzing apparatus including: a hemodialyzer comprising a container having an internal space and a semipermeable membrane accommodated in the internal space of the container, through which blood flows; a blood tube connecting between the hemodialyzer and a patient; a blood pump disposed on the blood tube to transfer blood; a dialysate tube in which dialysate flows; a dialysate pump supplying dialysate to the hemodialyzer and collecting used dialysate; and a temperature-based dialysate regeneration device regenerating the dialysate. The temperature-based dialysate regeneration device may include a JT refrigerator having a compressor, a condenser, an expander, and an evaporator, an adsorbent column to remove waste from dialysate, and a thermostat that regulates dialysate temperatures.

The refrigerant pressurized and heated by the compressor is primarily cooled while passing through the condenser, and expanded while passing through the expander. At this time, the refrigerant is changed to be in a more cooled (low temperature) state by Joule-Thomson effect. The cooled refrigerant passing through the evaporator may collect heat and then is re-supplied to the compressor, which repeats a refrigeration cycle.

The used dialysate discharged from the hemodialyzer may lose the heat, while passing through the other side of the evaporator, to be changed into a low temperature dialysate. After that, waste may be removed by adsorption, while the dialysate is passing through the adsorbent column. The dialysate having passed through the adsorbent column may be adjusted to have a temperature required for a hemodialysis treatment by the thermostat and supplied to the hemodialyzer by the dialysate pump.

The temperature-based dialysate regeneration device according to an embodiment of the present invention may further include a dialysate heat exchanger to perform heat-exchange between the dialysate extracted from the hemodialyzer and the adsorbent column to enhance heat transfer between the dialysate and the JT refrigerator. The refrigerant used for the JT refrigerator may be a mixture of two or more refrigerants to enhance the heat transfer generated by the latent heat in the evaporator and the condenser.

The temperature-based dialysate regeneration device according to an embodiment of the present invention may allow a small amount of dialysate to be recycled to thus exclude the use of a large amount of tap water while saving the treatment cost, thereby providing a small-sized blood dialyzing apparatus.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Hereinafter, a temperature-based dialysate regeneration device and a blood dialyzing apparatus including the temperature-based dialysate regeneration device according to an embodiment of the present invention will be described in detail with reference to the accompanying drawings.

In the following description of the present invention, the size, shape or the like of constituent elements illustrated in the drawings may be exaggerated or simplified for clarity and convenience of explanation. Also, the terms particularly defined taking into consideration the configurations and operations of the present invention may be changed based on the intentions of users or operators, or customs. These terms should be construed as meanings and concepts conforming to the technical spirt of the present invention based on the general context of this specification.

Figure 1:
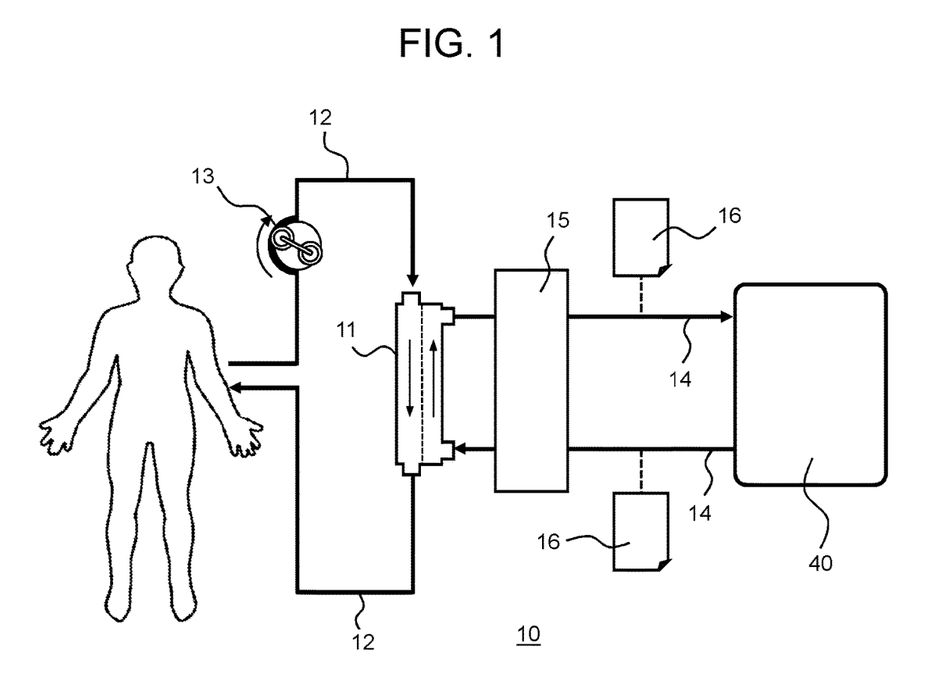
FIG. 1 is a view illustrating a blood dialyzing apparatus according to an embodiment of the present invention.

As shown in FIG. 1, a blood dialyzing apparatus 10 includes a hemodialyzer 11 comprising a container having an internal space and a semipermeable membrane accommodated in the internal space of the container through which blood flows, a blood tube 12 connecting between the hemodialyzer and a patient, a blood pump 13 disposed on the blood tube to transfer blood, a dialysate tube 14 connected to the hemodialyzer in which dialysate flows, a dialysate pump 15 supplying dialysate to the hemodialyzer and collecting used dialysate, a dialysate reservoir 16 storing dialysate, and a temperature-based dialysate regeneration device 40 regenerating the used dialysate having passed through the hemodialyzer.

Figure 2:
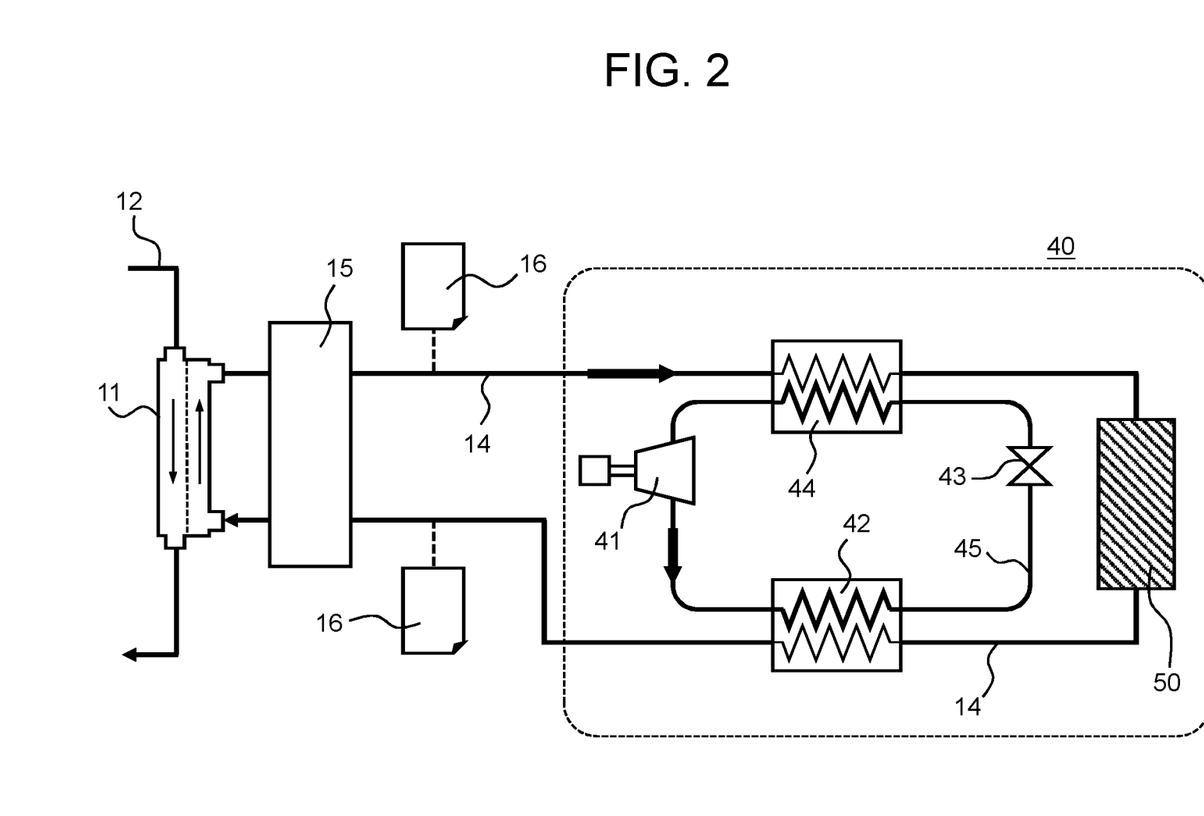
FIG. 2 is a view illustrating the temperature-based dialysate regeneration device including JT refrigerator having a compressor, a condenser, an expander, an evaporator, and an adsorbent column.

The temperature-based dialysate regeneration device 40 shown in FIG. 2 includes a compressor 41 compressing a refrigerant, a condenser 42 condensing (that is, cooling) the refrigerant pressurized by the compressor, an expander 43 expanding the refrigerant having passed through the condenser, an evaporator 44 where the refrigerant having passed through the expander collects heat, a refrigerant pipe 45 connecting the compressor, the condenser, the expander and the evaporator with each other, the refrigerant pipe 45 in which the refrigerant flows, and an adsorbent column 50 for removing uremic toxins contained in the dialysate.

The refrigerant is pressurized (high-pressure) and heated (high-temperature) during the compression by the compressor 41, and it is converted into a high-pressure and medium-temperature refrigerant after losing heat while passing through the condenser 42. When the refrigerant is expanded through the expander 43, the refrigerant is depressurized into a low-pressure refrigerant. In this case, the reduction in the refrigerant pressure results in the reduction in the refrigerant temperature to a low temperature, which is referred to as Joule-Thomson (JT) effect. Finally, the low-pressure and low-temperature refrigerant collects heat while passing through the evaporator 44, and then it flows into the compressor 41. These processes are repeated to form a closed-loop refrigeration cycle.

Thus, the refrigerant remains pressurized due to the compression by the compressor 41 through the condenser 42. On the contrary, the refrigerant is depressurized at the expander 43 and remains in a low-pressure state in the evaporator 44. Also, the refrigerant is heated when pressurized such that the temperature of the refrigerant at the outlet of the compressor may be the highest temperature. The refrigerant is cooled while passing through the condenser 42 and the expander 43. After passing through the expander 43, the pressure of the refrigerant is lowered and the temperature thereof is lowered simultaneously to be the lowest temperature, which is referred to as Joule-Thomson effect.

Here, the pressures and temperatures of the refrigerant at each point of the JT refrigeration cycle are not fixed values, but variable based on the type and flow rates of the refrigerant, the compression ratio of the compressor, or the capacity of the evaporator. The high pressure and the low pressure used in describing the refrigerant pressures and the high temperature, the medium temperature and the low temperature used in describing the refrigerant temperatures should be understood as expressions for relatively describing the pressures and the temperatures of the refrigerant in the elements comprising the refrigeration cycle.

Various types of expanders configured to lower the pressure of the refrigerant may be used. The exemplary expander 43 may include a valve expander and a capillary expander. The valve expander adjusts opening of a valve and determines an expansion ratio of refrigerant. On the other hand, the capillary expander regulates the expansion ratio by adjusting the length of a capillary. Likewise, various types of compressors may be used as a means of compressing refrigerant, such as a rotary type, a scroll type, and a linear type compressor. In addition, a micro-sized rotary compressor may be used to meet the objectives of the temperature-based dialysate regeneration device according to an embodiment of the present invention such that the dialysate regeneration device and the blood dialyzing apparatus can be small-sized. The compression ratio may be determined in consideration of the flow rate of the refrigerant, an expansion ratio of the refrigerant in the expander 43 and the heat transfer rate in the evaporator 44.

Hereinafter, the flow of dialysate according to an embodiment of the present invention will be described in detail with reference to the accompanying drawings.

As shown in FIG. 2, the used dialysate passing through the hemodialyzer 11 is cooled while passing through the other side of the evaporator 44 by the heat transfer with refrigerant thereof and then waste is removed from the dialysate by adsorption at the adsorbent column 50. The adsorption column 50 may be filled with various kinds of adsorbents, including activated charcoal and anion exchange resin, and two ore more kinds of adsorbents may be used together.

The activated charcoal can usually capture various-sized molecules through physical adsorption. However, small-sized molecules like urea nitrogen that is a waste product of protein metabolism in a body and is contained largely in the used dialysate have a low adsorption efficiency achieved by the activated charcoal when the adsorption occurs at room temperature. However, the adsorption efficiency of the small-sized molecules increases when the temperature for the adsorption is lowered, which is referred to as a cold adsorption. For example, when dialysate having a temperature of 28-32° C. flows through the activated charcoal, the urea nitrogen adsorption ratio of the activated charcoal is approximately 40%. However, when the dialysate temperature decreases to 0-5° C., the urea nitrogen adsorption increases up to 80% or more.

Thus, the dialysate needs to be cooled so that the adsorptive removal of uremic toxins contained in the dialysate can be enhanced through the adsorption column 50. The dialysate temperature required for hemodialysis treatment is typically kept as a body temperature of a patient. Accordingly, the dialysate at the outlet of the hemodialyzer 11 has a temperature of approximately 36° C. The dialysate temperature decreases when the dialysate passes through the evaporator 44, as shown in FIG. 2. As long as there is no risk of ice-making, it is preferred that the temperature of the dialysate can be adjusted as low as possible so as to remove various molecules contained in the dialysate using cold adsorption. The dialysate temperature required for the cold adsorption by the temperature-based dialysate regeneration device according to an embodiment of the present invention may be between −2° C. and 12° C.

Figure 3A:
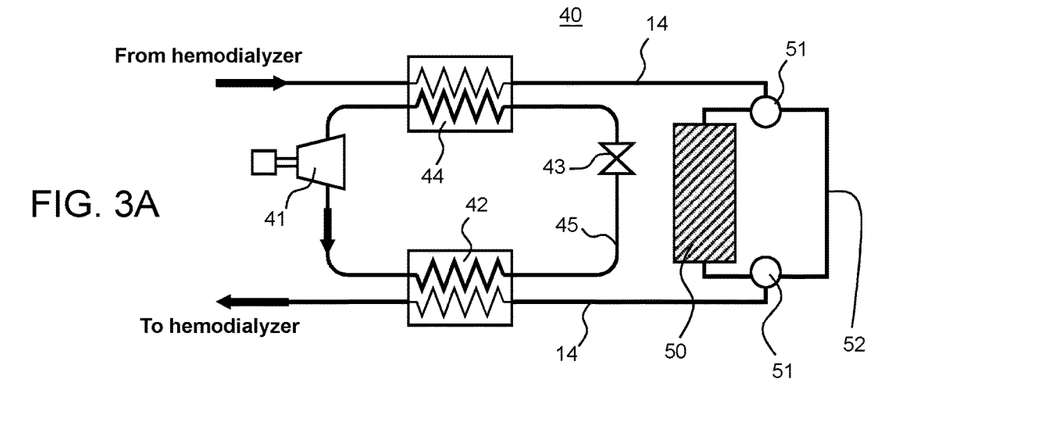
FIGS. 3A and 3B are views illustrating the adsorbent column and a bypass dialysate tube of the temperature-based dialysate regeneration device.
Figure 3B:
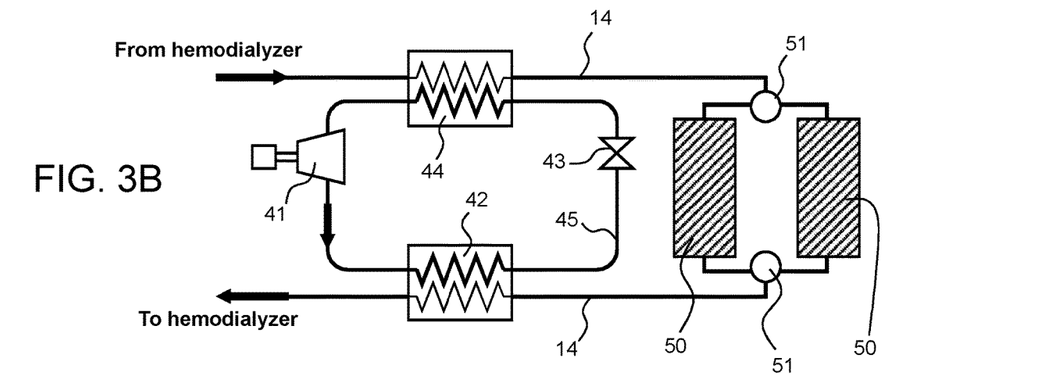

The adsorbent column 50 may be detachable and replaceable before and after hemodialysis or even during the hemodialysis. As shown in FIG. 3A, a bypass dialysate tube 52 may be provided in parallel to the adsorbent column 50 and a flow valve 51 may be disposed between the adsorbent column 50 and the bypass dialysate tube 52 to control a dialysate passage. When the adsorbent column 50 is mounted, the flow valve 51 allows the dialysate to flow to the adsorbent column 50. On the other hand, when the adsorbent column 50 is demounted, the dialysate may be directed to flow to the bypass dialysate tube 52. In addition, as shown in FIG. 3B, two adsorbent columns 50 may be used, and when one of the adsorbent columns is demounted, the dialysate may be allowed to flow to the other mounted adsorbent column by the flow valve 51.

In this instance, ultrapure water having a temperature of 80~98° C. may flow through the adsorbent column 50 where dialysate is not flowing so as to perform wet cleaning for the adsorbent. The adsorption efficiency by the adsorbent such as the activated charcoal significantly increases in a low temperature. Using such phenomenon reversely, when ultrapure water having a temperature of 80~98° C. flows through the adsorbent column, the captured molecules flows out from the adsorbent. Using such the adsorption capacity of the molecules variable based on a temperature, a low temperature dialysate may flow through the adsorbent and small-sized molecules contained in the dialysate are removed from the dialysate by the contact with adsorbent. Then, a high temperature ultrapure water flows through the adsorbent and the molecules adsorbed on the adsorbent may be detached therefrom and flow out. Accordingly, the adsorbent can be washed and reused. The adsorbent column reuse may be dependent on the environment of the hemodialysis where the adsorbent column is used, such as the amount of the uremic toxins which should be removed, the dialysate flow rates, and so on. For example, supposing a patient having a weight of 70 kg performs hemodialysis for 4 hours, three times a week, the adsorbent column 50 can be reused approximately 500 times.

The cold dialysate having passed through the adsorbent column 50 has to be reheated prior to entering the hemodialyzer to meet the objective of the hemodialysis, and various methods may be used to reheat the cold dialysate. As shown in FIGS. 2, 3A and 3B, the dialysate having passed through the adsorbent column 50 may collect heat through heat exchange with the refrigerant in the condenser 42, which is advantageous in that the heat exchange between dialysate and refrigerant through the condenser excludes an auxiliary process of cooling the refrigerant, thereby providing a simpler refrigeration cycle.

Figure 4A:
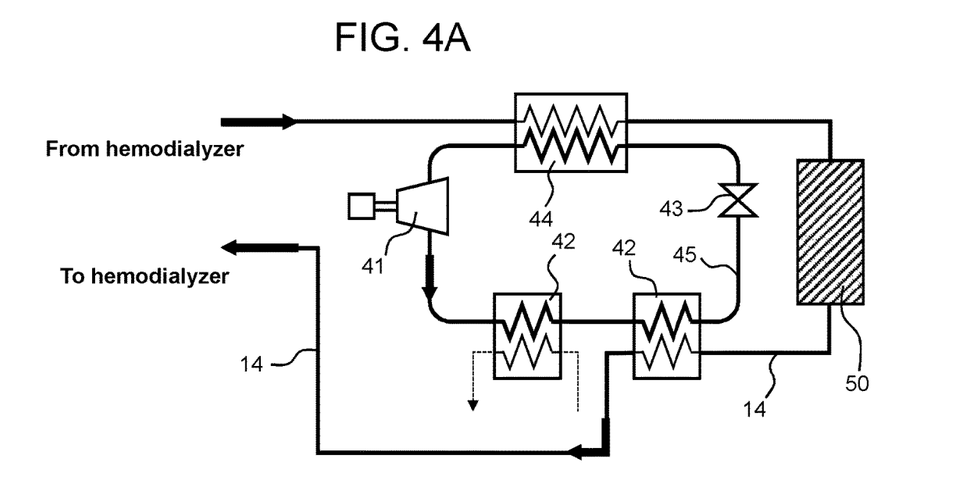
FIGS. 4A, 4B, 5A to 5C, and 6A to 6C are views illustrating the temperature-based dialysate regeneration device according to an embodiment of the present invention.
Figure 4B:
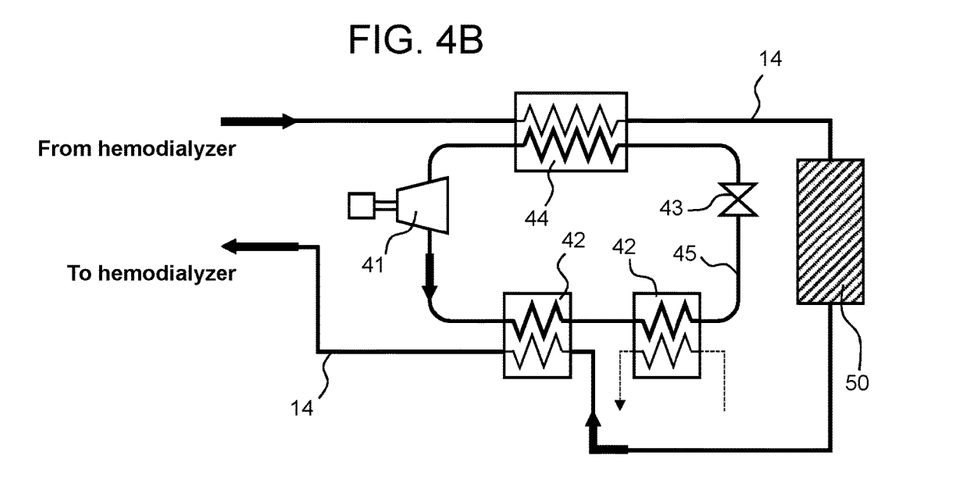

As shown in FIGS. 4A to 4C, the temperature-based dialysate regeneration according to an embodiment of the present invention may be provided with a plurality of condensers 42. Diverse types of condensers capable of cooling the refrigerant, while keeping the refrigerant pressure from being lost, may be used as the condensers 42. For example, an air-cooled condenser configured to use a fan in cooling, a water-cooled condenser configured to use water in cooling and an evaporation-cooled condenser configured to use latent heat for vaporization of a fluid may be used as the condensers 42.

Figure 5A:
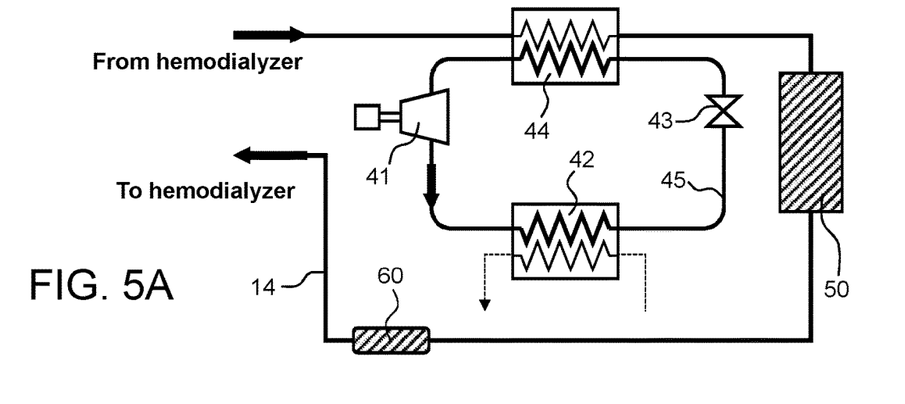
Figure 5B:
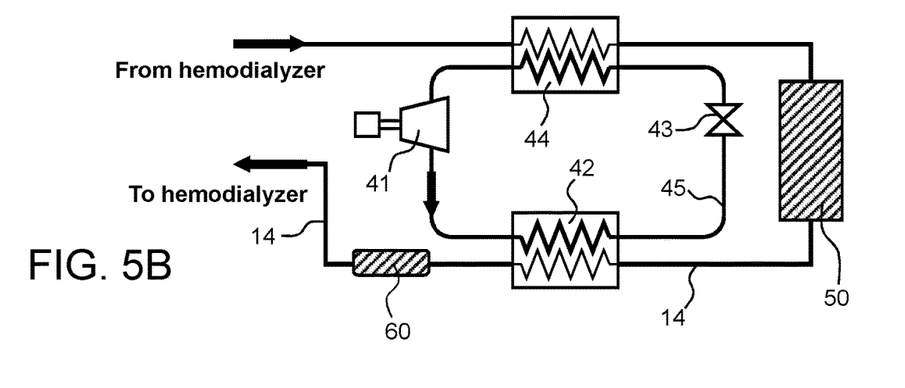
Figure 5C:
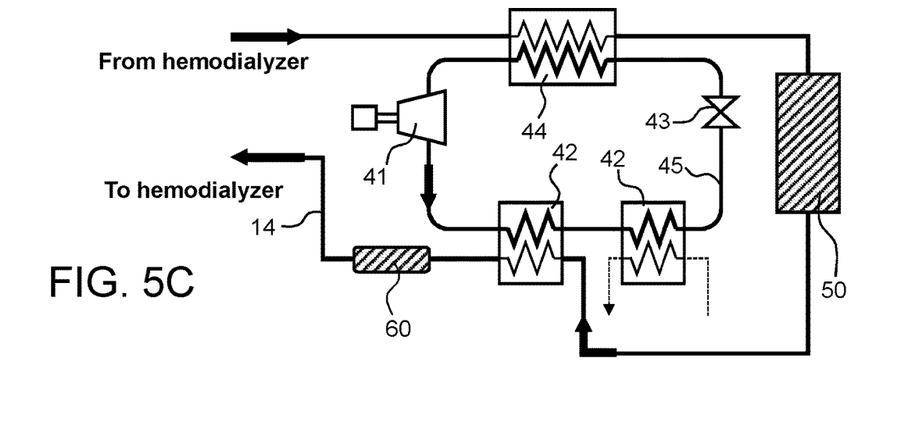

In addition, according to an embodiment of a present invention, a thermostat 60 may be further provided to adjust the dialysate temperature. FIGS. 5A to 5C are flow circuit diagrams of the temperature-based dialysate regeneration device, which are configured to include the thermostat 60. Various types of thermostats may be used for the thermostat 60, including a water-cooled thermostat, electrical thermostat, or a Peltier element.

After the dialysate temperature is adjusted to a preset temperature required for hemodialysis, the dialysate is supplied to the hemodialyzer 11 by the dialysate pump 15. Since an electrolyte concentration of dialysate could be changed while passing through the adsorbent column 50, it is preferred that there is an ion balancing step to measure and adjust an electrolyte concentration of the dialysate before the dialysate is supplied to the hemodialyzer 11.

Various types of heat exchangers may be used as the evaporator 44 and the condenser 42. Examples of the heat exchangers may include a double-pipe heat exchanger capable of achieving a high amount of heat transfer, even with a small size. The heat transfer rate (q) of the dialysate in the evaporator and the condenser may be calculated by a following formula:

$$q = m * C_p * T \quad (1)$$

The dialysate is produced of ultrapure water and it can be regarded as water in a thermodynamic perspective (Cp=4.18J). Supposing that dialysate flows at the rate of 500 ml/min (m=8.33 g/s) and the dialysate temperature decreases from 36° C. to 1° C., i.e., by 35 degrees, 1,219 Watt of heat transfer is required through the evaporator, according to Equation 1. In other words, 1,219 Watt heat is transferred to the refrigerant from the dialysate. It is preferred that the size of the evaporator 44 and the condenser 42, and refrigerant flow rates therethrough may be determined considering such the heat transfer quantity.

Figure 6A:
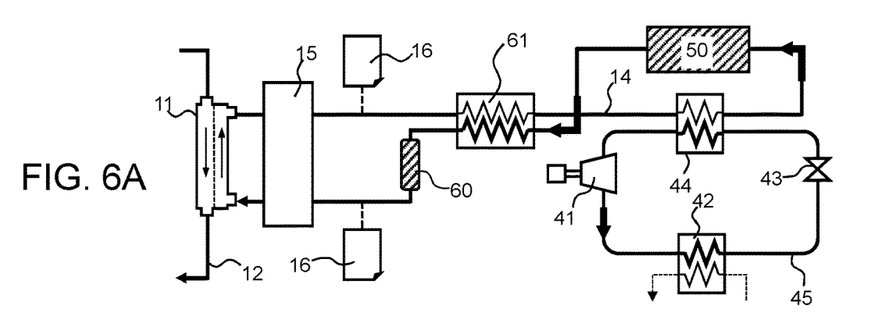
Figure 6B:
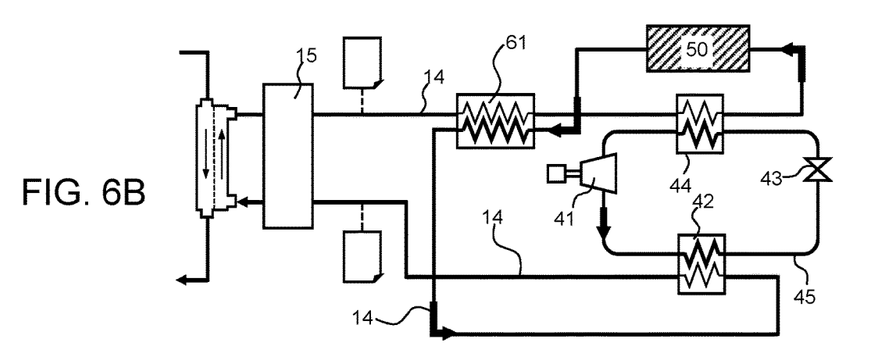
Figure 6C:
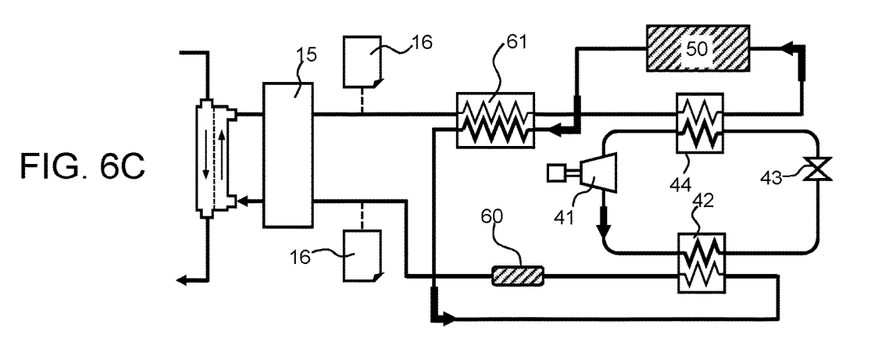

The temperature-based dialysate regeneration device according to an embodiment of the present invention, as shown in FIGS. 6A to 6C, may further include a dialysate heat exchanger 61 configured to perform heat exchange between the dialysate discharged from the hemodialyzer 11 and the dialysate having passed through the adsorbent column 50. The dialysate heat exchanger 61 may provide two advantages. First, the dialysate heat exchanger 61 may cool the dialysate flowing into the evaporator 44 and decrease the required heat transfer load in the evaporator, which is also referred to as a refrigeration load, such that the overall size of the JT refrigerator can be further decreased. Second, the low temperature dialysate having passed through the adsorbent column 50 may collect some of the heat in the dialysate heat exchanger 61 such that the heating load of the thermostat 60 can be decreased.

As shown in FIGS. 6B and 6C, after the dialysate having passed through the adsorbent column 50 collects some of heat in the dialysate heat exchanger 61, the dialysate temperature may be adjusted to the temperature required for hemodialysis by the heat exchange with the refrigerant in the condenser 42. For example, the dialysate temperature at the outlet of the hemodialyzer 11 is supposed to be 36° C. and it needs to be 0° C. at the inlet of the adsorption column 50. Supposing that the heat exchanger 61 is insulated and the dialysate temperature is changed by 26° C. while passing through the heat exchanger 61, the dialysate temperature flowing into the evaporator 44 may be 10° C. and it is cooled down to 0° C. through the evaporator 44. In other words, 10° C. of dialysate temperature change occurs in the evaporator. Then, dialysate at 0° C. passes through the adsorbent column 50 and the other side of the heat exchanger 61. Dialysate gains heat and becomes 26° C., when it passes through the other side of the heat exchanger. Finally, the dialysate may be further heated by the heat exchange with the refrigerant in the condenser 42 to become the temperature required for the hemodialysis. In this case, the thermostat 60 may be further provided to adjust the temperature of the dialysate having passed through the condenser 42.

According to an embodiment of the present invention, the JT refrigerator may use not only CFC (chlorofluorocarbon), HCFC (hydrochlorofluorocarbon) or HFC (Hydrofluorocarbons)-based single component refrigerants (e.g., R12, R22 and R134a), but also a mixture of HFC, HCFC or HC (hydrocarbon) refrigerants. Using a mixed refrigerant (MR), the heat transfer in the condenser 42 and the evaporator 44 may be enhanced by the latent heat transfer of the mixed refrigerant.

Figure 7:
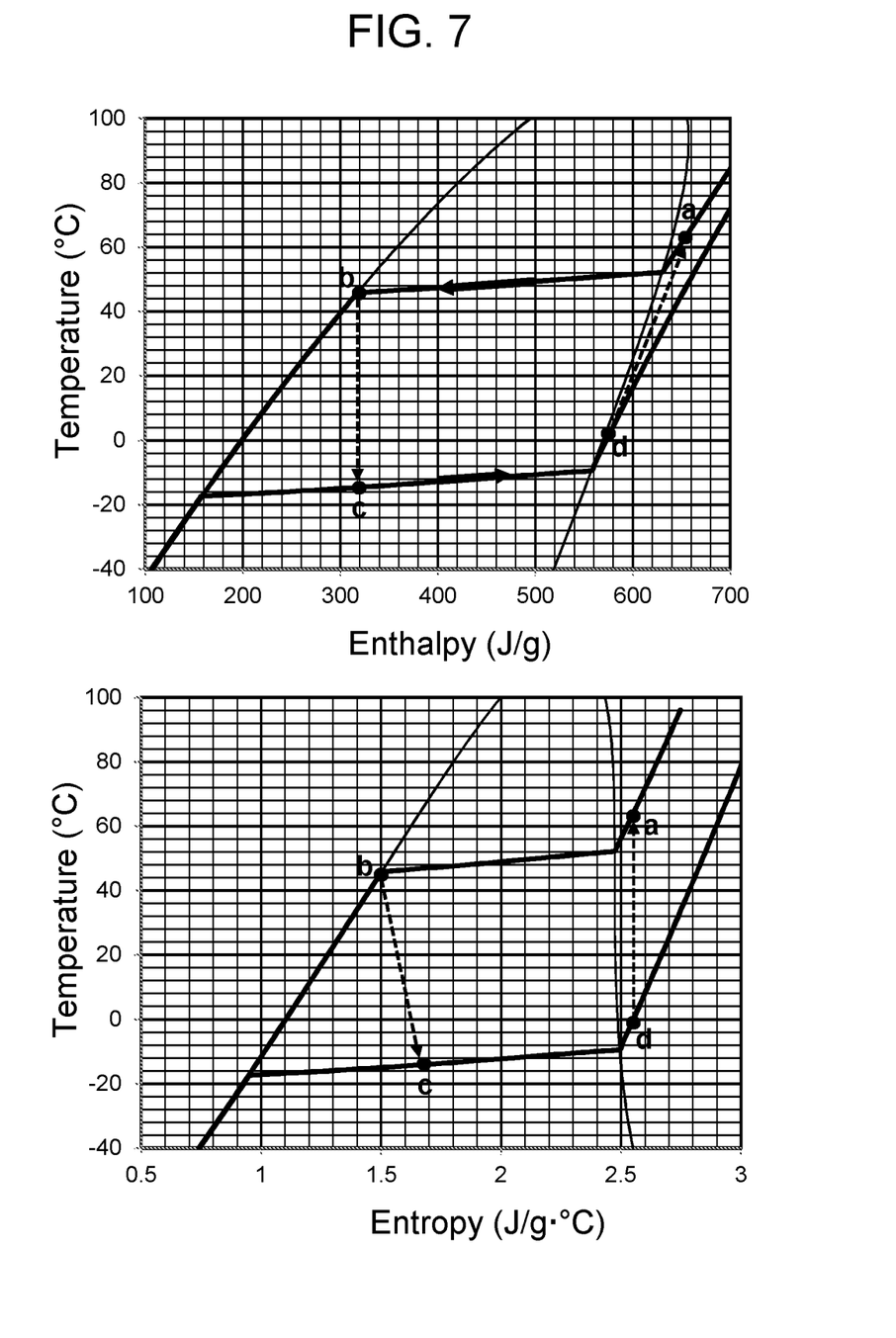
FIG. 7 is a view illustrating the temperature-enthalpy and temperature-entropy diagram of the mixed refrigerant composed of Propane, R143a, and Iso-butane at the mass ratio of 40%, 20% and 40%.

FIG. 7 shows the result of temperature-enthalpy and temperature-enthalpy simulation, in case a refrigerant having Propane, R143a and Iso-butane by a mass ratio of 40%, 20% to 40% is used as the refrigerant for the JT refrigerator. Refrigerant pressures before and after compression were assumed as 0.2 MPa and 1.2 MPa, respectively, such that a compression ratio is 6. Pressure loss of the refrigerant in the condenser 42 and the evaporator 44 is ignored. Here, d-a refers to a compression process and a-b refers to a condensation process. B-c refers to an insulation expansion and c-d refers to an evaporation process. Wide enthalpy change can be achieved due to a phase-change during condensation and evaporation. The heat transfer rate during phase-change can be defined as the value multiplied by a mass flow rate of the refrigerant and an enthalpy change. Since the mixed refrigerant has a high enthalpy change during a phase-change, the required refrigerant flow rate may be kept to a minimum to achieve the same heat transfer rate, which leads to the decrease in the capacity of the compressor 41 and ultimately the size of the refrigerator.

Hereinafter, the operation of the blood dialyzing apparatus 10 including the temperature-based dialysate regeneration device 40 according to an embodiment of the present invention will be described in detail with reference to the accompanying drawings.

Blood passes through the hemodialyzer 11 by the blood pump 13 and dialysate passes through the hemodialyzer 11 and then is discharged by the operation of the dialysate pump 15. The blood and dialysate flow through a blood flow region and a dialysate flow region of the hemodialyzer, respectively. In addition, the blood dialyzing apparatus 10 may further include a dialysate reservoir 16 to store dialysate.

The used dialysate having passed the hemodialyzer is cooled while passing through one side of the dialysate heat exchanger 61 provided in the temperature-based dialysate regeneration device 40. Dialysate is further cooled to the temperature required for the cold adsorption, while passing through the evaporator 44. The uremic toxins and waste are removed from the cold dialysate while passing through the adsorbent column 50, and the dialysate collects heat while passing through the other side of the dialysate heat exchanger 61. After the temperature of the dialysate is finally adjusted to be the temperature required for the hemodialysis through the condenser 42, the dialysate is supplied to the hemodialyzer 11. Here, an ion balancing step may be preferably provided to adjust the electrolyte concentration of the dialysate, before the dialysate having passed through the adsorbent column 50 is supplied to the hemodialyzer 11.

The temperature-based dialysate regeneration device 40 according to an embodiment of the present invention is not limited to perform the regeneration of the used dialysate. In the case of hemofiltration which is a process of removing excessive water from blood due to fluid suction by the dialysate pump 15, the temperature-based dialysate regeneration device may also be used to regenerate filtration fluid. The quantity of the filtration removed from the blood in a typical hemofiltration treatment is remarkably larger than the quantity of the actual amount of excessive water that has to be removed from a patient. That is because various uremic toxins can be removed together with the filtration. In other words, uremic toxin clearance is proportional to the filtration quantity. However, it is evident that the far larger amount of filtration causes a patient's serious dehydration, and thus supplementary solution should be supplied to compensate the dehydration. However, the temperature-based dialysate regeneration device according to the present invention may continuously regenerate the filtration fluid and re-supply it to a patient, thus removing the requirement of providing a supplementary solution infusion. Accordingly, the overall structure of the hemofiltration device may be substantially simplified while reducing the treatment cost. Here, the dialysate reservoir 16 may be used to store filtration fluid.

In the hemodialysis or hemofiltration device including the temperature-based dialysate regeneration device according to the present invention, a small amount of dialysate or filtration fluid may be continuously regenerated using the mixed refrigerant JT refrigerator and the adsorbent column 50. Accordingly, the use of a large amount of tap water may be excluded and the hemodialysis or hemofiltration device can be small and light-weighted.

Embodiments of the present invention described above and illustrated in the drawings should not be construed as limiting the technical spirit of the present invention. The scope of the present invention should be defined as disclosed in the accompanying claims, and those skilled in the art will appreciate that various modifications, additions and substitutions are possible without departing from the scope and spirit of the invention.

What is claimed is:

1. A temperature-based dialysate regeneration device for regenerating dialysate, comprising:
   a compressor compressing refrigerant;
   a condenser cooling the refrigerant pressurized by the compressor;
   an expander expanding the refrigerant having passed through the condenser;
   an evaporator where the refrigerant having passed through the expander collects heat from the dialysate;
   an adsorbent column removing waste from the dialysate; and
   a dialysate heat exchanger performing heat exchange between the dialysate discharged from a hemodialyzer and the dialysate having passed through the adsorbent column.

2. The temperature-based dialysate regeneration device of claim 1, comprising a thermostat adjusting a temperature of the dialysate.

3. The temperature-based dialysate regeneration device of claim 1, comprising an ion balancer measuring and adjusting an electrolyte concentration of the dialysate.

4. The temperature-based dialysate regeneration device of claim 3, wherein the refrigerant passing through the compressor, the condenser, the expander, and the evaporator is a mixture of two or more refrigerants.

5. The temperature-based dialysate regeneration device of claim 3, wherein the adsorbent column is detachable.

6. The temperature-based dialysate regeneration device of claim 3, wherein the dialysate having passed through the adsorbent column collects heat through heat exchange with the refrigerant at the condenser.

7. The temperature-based dialysate regeneration device of claim 3, wherein the refrigerant passing through the compressor, the condenser, the expander, and the evaporator repeats a close-loop cycle.

8. The temperature-based dialysate regeneration device of claim 3, wherein the dialysate flowing into the adsorbent column has a temperature of −2~12° C.

9. A blood dialyzing apparatus, comprising:
   a hemodialyzer including a container having an internal space and a semipermeable membrane accommodated in the internal space of the container, the hemodialyzer through which blood flows;
   a blood tube connecting between the hemodialyzer and a patient to allow blood to flow therethrough;
   a blood pump disposed on the blood tube to transfer blood;

a dialysate pump supplying and discharging dialysate or filtrate; and a temperature-based dialysate regeneration device according to claim 3 removing toxins and waste from the dialysate or the filtrate to regenerate the dialysate or the filtrate.

10. The blood dialyzing apparatus of claim 9, further comprising a reservoir storing the dialysate or the filtrate.

11. The blood dialyzing apparatus of claim 1, wherein the dialysate or the filtrate flowing into the adsorbent column has a temperature of −2~12° C.

12. The temperature-based dialysate regeneration device of claim 2, comprising an ion balancer measuring and adjusting an electrolyte concentration of the dialysate.

13. The temperature-based dialysate regeneration device of claim 12, wherein the refrigerant passing through the compressor, the condenser, the expander, and the evaporator is a mixture of two or more refrigerants.

14. The temperature-based dialysate regeneration device of claim 12, wherein the dialysate flowing into the adsorbent column has a temperature of −2~12° C.

* * * * *